United States Patent [19]
Chvapil et al.

[11] Patent Number: 5,227,168
[45] Date of Patent: Jul. 13, 1993

[54] METHOD OF TREATING A WOUND

[75] Inventors: Milos Chvapil, Tucson, Ariz.; Bruce Barber, 77 Duck Hill Rd., Duxbury, Mass. 02331

[73] Assignee: Bruce Barber, Duxbury, Mass.

[21] Appl. No.: 887,357

[22] Filed: May 21, 1992

Related U.S. Application Data

[62] Division of Ser. No. 742,319, Aug. 8, 1991, Pat. No. 5,116,620, which is a division of Ser. No. 439,472, Nov. 21, 1989, Pat. No. 5,104,660.

[51] Int. Cl.$^5$ .............................................. A61L 15/00
[52] U.S. Cl. .................................... 421/445; 424/443; 424/444; 424/446; 424/448; 424/449
[58] Field of Search ............... 424/445, 443, 444, 446, 424/448, 449

[56] References Cited

U.S. PATENT DOCUMENTS

| | | | |
|---|---|---|---|
| 4,035,483 | 7/1977 | Bunyan | 424/149 |
| 4,330,531 | 5/1982 | Alliger | 424/149 |
| 4,681,739 | 7/1987 | Rosenblatt et al. | 422/39 |
| 4,917,895 | 4/1990 | Lee et al. | 424/448 |

Primary Examiner—Thurman K. Page
Assistant Examiner—Leon R. Horne
Attorney, Agent, or Firm—Richard P. Crowley

[57] ABSTRACT

An antimicrobial wound dressing and method of wound treatment, the wound dressing having a layer of a collagen dressing material impregnated with lyophilized, stabilized chlorine-containing compounds which generate on activation chlorine dioxide, like a mixture of sodium chlorate and sodium chlorite, and an adjacent layer secured thereto containing a dry, activating amount of an acidic compound, such as citric acid, whereby moisture from the wound activates the dry chlorine moiety to treat the wound.

8 Claims, 1 Drawing Sheet

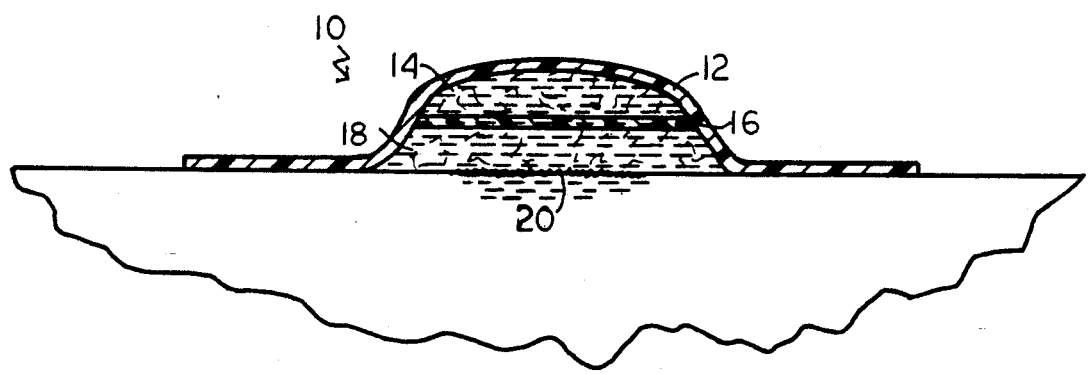

METHOD OF TREATING A WOUND

REFERENCE TO PRIOR APPLICATIONS

This application is a divisional application of U.S. Ser. No. 07/742,319, filed Aug. 8, 1991, now U.S. Pat. No. 5,116,620 which is a divisional of U.S. Ser. No. 07/439,472, filed Nov. 21, 1989, now U.S. Pat. No. 5,104,660.

BACKGROUND OF THE INVENTION

Wound infection followed by a breakdown of surgical or traumatic wounds still remains in the forefront of wound care, despite several available measures to prevent this complication of wound healing, often threatening the life of the patient.

It has been documented that if the bacterial counts in the wound exceed $10^5$ organisms/1 gram of the wound tissue, the infection is a serious problem that without proper medical attention results in systemic sepsis. Microorganisms infect wounds originating either from within the human body, which is a known reservoir for pathogenic organisms, or from environmental origin (military wounds). The most common microorganisms are *S. aureus, St. epidermis*, beta haemolytic Streptococci, *E. coli*, Klebsiella and Pseudomonas species and among the anaerobic bacteria, the *Clostridium welchii* or *tartium*, which are the cause of gas gangrene, mainly in deep traumatic wounds.

It is quite understandable that through the history of wound care, several methods and drugs were tested and used to prevent or reduce the risk of infected wounds. Generally, it can be said that many of the antimicrobial treatments adversely affect the wound and the treatment becomes toxic not only to microorganisms but also to the cell-wound tissue. Another limitation is that many treatments affect only the surface of the wound while some common bacteria (Pseudomonas) quickly merge into the repair tissue, forming multiple foci with puss. This is a situation that occurs with very popular drugs based on silver, iodine and cerium, which link actively with proteins of the wound tissue without diffusing deep enough through the wound to reach the microorganism.

Antibiotics, both systemically or topically administered, represented a milestone in the treatment of infected wounds. However, antibiotics, per se, may represent another "toxic" burden to a patient with multiple injuries, deep burns over a large body area, or where the liver function is stressed by the wound toxins. Only topical administration of antibiotics may result in formation of bacterial strain resistant to additional treatment with antibiotics.

SUMMARY OF THE INVENTION

The present invention relates to an antimicrobial wound dressing and to the method of manufacturing and to the method of treating a wound by the use of the wound dressing.

The antimicrobial wound dressing of the invention comprises a multiple layer, preferably a two-layer, dressing with one layer retaining material impregnated with an effective, but antimicrobial amount of a freeze-dried, stabilized, chlorine-containing compound which on activation generates chlorine dioxide in situ as an active ingredient, either alone or with other antimicrobial materials, while another adjoining but separate layer comprises a retaining material impregnated with a pharmaceutically-accepted, activating compound, such as a dry, acidic compound in an activating amount for the chlorine compound. The acidic compound when placed in contact with the freeze dried or lyophilized chlorine-containing compound and in the presence of moisture from the wound or externally applied provides for the in situ generation of strong oxidizing chlorine dioxide and hypochlorite for the treatment of the wound. Generally, the adjacent layer surfaces are secured together, such as by the employment of a water permeable, adhesive, and optionally and preferably, an outer barrier, water and gas impervious, covering layer is employed, such as low vapor permeable material to limit the drying of the wound to be treated to which the wound dressing is to be applied.

The method of manufacturing the novel wound dressing of the invention comprises impregnating a first retaining, sheet type material, such as sponge type material, with an antimicrobial amount of a stabilized chlorine compound containing solution and thereafter freeze drying or lyophilizing the impregnated sheet material to provide dry, chlorine moieties, impregnated sheet material; and impregnating a second retaining sheet material which may be the same or different material than the first material with an effective, activating amount of an activator acidic compound, which is pharmaceutically acceptable, such as a low molecular weight, non-toxic, organic acid, such as boric acid, citric acid or ascorbic acid, typically by impregnating the retaining material with a solution of the acid and thereafter, freeze drying or lyophilizing to obtain a retaining material impregnated with the acidic activator compound. The method optionally includes securing the first chlorine based retaining material as a separate layer to the second dry retaining material impregnated with the dry, acidic, activator compound, such as by adhesively securing the layers together with a water permeable layer, and also optionally, providing a cover barrier sheet over the one top surface of the dry, acidic, activated compound which forms the upper layer of the wound dressing to prevent the drying out of the wound, and optionally, but preferably, sterilizing the multi-layered wound dressing so prepared.

In use, the wound dressing is placed over the wound by the use of adhesive tape or the adhesive tape may be a portion of the top covering surface with the dry, stabilized, chlorine-containing compounds and the impregnated retaining material placed adjacent the wound. The moisture in the wound provides together with the dry, acidic, activator compound and the dry, stable, active components, the conditions for the generation of a strong oxidizing and antimicrobial effect of chlorine dioxide and hypochlorite from the lower layer of the retaining material so as directly to treat in situ and disinfect the wound.

The retaining materials employed in the upper layer of the wound dressing may be the same or different, and typically, such material comprises a soft, flexible, porous type material suitable for use in contact with the wound and used as a wound dressing to include, but not be limited to: natural materials, such as collagen sponge; open cell foam materials, such as natural and artificial rubber and urethane type foam materials; membrane materials; woven or non-woven fabrics made of natural or synthetic materials; or any other material or substance which can retain the dry, impregnated, stabilized chlorine-containing compounds and the dry, impregnated acidic activator compounds as desired. A separate layer of the dry active-oxidizing, moiety-producing compounds and the dry activator compound typically are secured together by an adhesive layer, but does not prevent the moisture activation of the dry, microbiologically active components from its function in the wound dressing.

The active ingredient in the lower layer is the freeze dried or lyophilized, chlorine-containing compounds, such as sodium chlorites, chlorous acid, chlorates, etc., which generate hypochlorite or chlorine dioxide, impregnated into the retaining material. However, other types of disinfecting drugs or antibiotics and other materials which do not interfere with the dry, lyophilized, chlorine-containing, stabilized compounds may be used in combination with the dry, lyophilized active components as desired. The acidic activator compound may comprise any activator which provides for a weak acidic pH in the presence of water or moisture so as to activate and convert the dry, lyophilized chlorine compounds into a strong, oxidizing moiety of chlorine dioxide or hypochlorite through the use of the activator compound. Generally, the activator compound should be topically, that is, dermatologically and pharmaceutically acceptable, for use on and about wound dressing. Particular compounds which can be used include: citric acid; ascorbic and tartaric acid; boric acid; and similar types of weak acid or other pharmaceutically-acceptable acid salts. Chemically weak organic acids are preferable, as these only destabilize the originally stable chlorine-containing compounds, thus inducing slow chemical reaction resulting in sustained, not explosive, formation of strong, oxidizing compounds such as $CLO_2$ or $CLO$.

The dimensions of the sheet material employed in the coverings as well as the concentrations of the various active and activator ingredients may of course vary as desired; however, for example, where a collagen sheet is employed as the dry chlorine compound retaining material, typically, such material would have a range of about 0.4 mm to 1.5 mm thick wherein the concentration of the stabilized chlorine dioxide would range from about 0.5 to about 1.5 weight percent of the retaining material. The other retaining layer may be of similar thickness and generally may comprise from about 2% to 7% by weight of an active acid solution prior to freeze drying.

The wound dressing may be packaged in a separate package or the activated layer containing the dry, stable chlorine components may be sealed using a removable, impermeable sealing strip which is removed prior to application to the wound or which may have perforations therein and be applied directly to the wound so the oxidizing chlorine and other formed compounds will pass through the perforations and into contact with the wound. Generally, the wound dressing should be sterilized by any known sterilization method technique, such as ethylene oxide or gamma radiation or other such techniques. Usually, but preferred, the retaining material for the freeze dried chlorine compounds should be typically pre-treated, such as by soaking the material, like the sponge or other collagen matrices, in a solution of stabilized chlorine-containing components in buffers with a pH of about 7.5 to 9.0 to prevent decomposition of the active substance.

The production of strong, oxidizing environment represented by chlorine-containing compounds occurs by interaction of substances, such as sodium chlorite, sodium chlorate, chlorous acid anion, with acid, such as citric acid, in a an aqueous medium. In order to prevent contact of these components with the wound dressing matrix and possible early decomposition of chlorine-containing compounds with time, a two layer system of wound dressing is used. The upper layer, i.e. the layer away from the wound surface, contains the acid moiety while the layer adjacent to the wound contains the dry chlorine compounds. Both layers consist of a dressing material, such as collagen sponge, approximately 0.4 mm to 1.5 mm thick, or collagen membrane, 0.3 mm to 0.5 mm thick, or any other preformed wound dressing material in a completely dry state. The dressing material is soaked with the appropriate chemical solution, quick frozen in a freezer at −70° C. and placed into a freeze dryer (lyophilizer) to evaporate the fluid. By this method, dry layers contain either active substances or the activating moiety, such as citric acid, at appropriate, effective concentrations.

The two layers are secured together for example, glued together, with a biocompatible adhesive, such as an acrylic adhesive. In order to limit the drying of the wound and to retain wound fluid within the wound dressing, the upper layer of the dressing is laminated or covered with any commercially available adhesive film that limits vapor permeability. Lamination also facilitates easy attachment of the dressing to cover the wound and intact skin. Examples such a laminating film or laminated self-adhesive, non-woven fabric are all polyurethane adhesive films available commercially. The requirement for such a laminating layer are biologic, non-toxic elements, hypoallergenic physical vapor permeation 0.5 mg–2.0 mg $H_2O/cm^2/hr$ and elasticity.

The lower layer of the dressing impregnated with the active ingredient chlorine-containing compound is activated in situ in the presence of an acid from the adjacent layer. On acidification of the active ingredient, stronger oxidizing substances are formed which exert a very effective cidal effect. Also, importantly, the rate of formation of the oxidizing substances from the active ingredient, i.e. the gaseous chlorine dioxide from the lyophilized chlorine compound, is pH dependent and may take hours at pH 6–7 and only seconds at 2–2.5. Sufficient weak, acid-like citric acid is used in the top layer to change the pH of the lower layer from the stabilized pH of 8.5–9.0 to 6 pH or less, e.g. 5–6 pH. The chlorine-containing compound in the lower layer is made stable with alkali buffer of low buffering capacity pH 8.5–9.0, like sodium bicarbonate and sodium borate, so that the pH may be easily changed by a weak acid to below 6.0 pH.

Aqueous solutions known as chlorine dioxide solution are commercially available; however, such solutions typically comprise a mixture of chlorate, chlorite and hydrochlorous acid alkali stabilized at a pH of 8.5–9.0, such as the sodium salts of such compounds. Such solutions generally are prepared by the reaction of chlorous acid and sodium bicarbonate. Such chlorine-containing, aqueous solutions comprise mixtures of 0.1% to 5.0% by weight of the solution with the mixtures, about 1% to 3% by weight of sodium chlorate, 9% or more of sodium chlorite and about 6% to 8% chlorous acid at a stabilized pH.

The quick freezing and additional freeze drying of the stabilized chlorine compounds containing solution is essential, as this moiety is temperature and light sensitive. It is also important to adjust the pH of the dressing material to 8.5-9.5 at which temperature there is no destabilization and decomposition of the active substance. Finally, the final product must be packaged in light and water vapor impermeable bags to obtain good shelf life of the product. Sterilization of the wound dressing so prepared is usually by gamma radiation, 1.5 to 2.5 Merads.

The invention will be described for the purposes of illustration only in connection with certain embodiments; however, it is recognized that various changes, modifications, additions and improvements may be made to the illustrated embodiments and examples, all without departing from the spirit and scope of the invention.

BRIEF DESCRIPTION OF THE DRAWING

The drawing is an illustrated, schematic, sectional view of a wound dressing of the invention applied to a wound.

DESCRIPTION OF THE EMBODIMENTS

The wound dressing 10 of the invention is composed of a first moisture-impermeable layer 12, a second collagen, citric acid activator impregnated layer 14, a third biocompatible, acrylic, moisture permeable adhesive layer 16, and a fourth collagen, chlorine compound, dry, impregnated layer 18, all layers laminated together and the wound dressing shown covering a wound 20.

EXAMPLE 1

Collagen sponge made by the method presented in U.S. Pat. No. 4,193,813 from Mar. 18, 1980 was used. The sponge was crosslinked and was therefore resilient when wet. The sponge existed as a sheet 0.8 mm thick. The original 3.0 pH of the sponge was changed to pH 8.0 by incubation in 0.5M phosphate buffer. The excess buffer was removed by mechanical force. Such a moist sponge binds 35 ml of fluid per 1 g of the sponge substance.

The sponge layers were soaked in a 1% solution of chlorine dioxide (DURA-KLOR, a trademark of RioLinda Chemical Co., Inc. of Sacramento, Calif.). When completely hydrated, they were individually frozen at $-70°$ C. in Revco deep freezer for two hours. Frozen layers were then placed in a Virtis freeze dryer, and under vacuum at low temperature, the fluid was removed from the sponge matrix.

The lyophilizer conditions were: original vacuum between 10 to 50 millitorrs, condenser temperature $-60°$ C., sheet was heated to 48° C. Completely dried sponges were kept in light impermeable plastic bags, refrigerated in dry atmosphere. Another set of sponges was soaked as such (without changing the pH) in 5 weight percent of citric acid solution. The same procedure was used to dry the sponges.

Two dry sponges, one containing chlorine-active compounds and the other containing citric acid were now glued together with adhesive Polytac 212 (H & N Chemical Company, New Jersey) by applying a thin layer of the adhesive to one side of either sponge layer. The adhesive fluid evaporated under light compression of the sponges. In the next step, an adhesive film, Tegaderm, was attached to the citric acid-containing sponge surface in such a way that the film made a 1.5 cm wide rim outside the area of the sponge.

The dry two-layer sponge dressing was placed and heat sealed into bags and sterilized with 2.5 Merads gamma radiation.

EXAMPLE 2

Example 2 shows the antimicrobial effectiveness of the Example 1 dressing in vitro system using *E. coli* grown on agar plate. The standard procedure used by microbiological labs was used. In principle, 2 cm diameter disks were cut off the dressing of Example 1. One disk was placed on agar which has been seeded with *E. coli* and placed in 12 cm wide sterile Petri dishes. After a defined incubation time, a clear area of no growth under or around the disk was determined as an indication of antibacterial activity of the chlorine-containing moiety in collagen sponge system. Once the disk of the final dressing is laced onto the *E. coli* inoculated agar, 2 ml of a culture media consisting of:
1. Soybean Case Digest Broth (SCDB)
2. Sabouraud's Dextrose Broth (SDB)
3. Soybean Case Digest Agar (SCDA)
4. Soybean Case Digest Agar with 5% sheep blood
5. Sabouraud's Dextrose Agar (SDA)
6. Sabouraud's Dextrose Agar with 5% sheep blood is added over the disk. These plates are then refrigerated overnight at 4° C.-5° C. to prevent diffusion of the chemical into the agar, prior to the incubation at 37° C. for 18-25 hours, permitting the bacterial growth. The presence of the diffused chemicals in the agar inhibits or completely blocks the bacterial growth is referred to as an inhibition zone.

The results of the test performed under the above conditions, with 24 hours incubation, showed a 10 cm to 11 cm wide inhibition zone. Thus, the bacteria grew only at the rim of the Petri dish. It was concluded that the antimicrobial dressing was most effective against the growth of *E. coli*.

EXAMPLE 3

Example 3 documents the changes in the antimicrobial activity of the wound dressing with time.

The same testing protocol as shown in Example 2 was used. In this study, the disks were incubated first in plain Petri dishes containing 10 μl of sterile saline placed on a slowly tilting platform (10 cycles/min). The disks were incubated for 0, 6, 12 and 24 hours, removed at three times from the dish and placed on agar inoculated with Staphylococcus aureus. The same procedure was used, viz., 24 hours incubation at 4° C. to allow diffusion of the active antimicrobial substance was followed by another 24 hours incubation at 37° C. All samples at each time period were tested in triplicates.

The results shown in Table I document that the collagen sponge wound dressing with the system described in Example 1 was effective even after 24 hours. The variability of the results (at 6 hours) is explained by sample variability.

TABLE I

| THE DURATION OF ANTIMICROBIAL EFFECTIVENESS OF THE MEDICATED COLLAGEN SPONGE DRESSING AGAINST *ST. AUREUS* GROWTH | |
|---|---|
| Time (hrs) | Zone Inhibition (cm) |
| 0 | 10 |
| 6 | 7.5 |
| 12 | 9 |
| 24 | 10 |

EXAMPLE 4

Example 4 documents the determination of the optimal dose of chlorine-containing moiety in the collagen sponge effectively killing bacteria without an adverse effect on the wound healing.

Collagen sponge dressing was prepared as shown in Example 1 except that the strength of original stabilized chlorine compounds containing solution soaking individual collagen sponges ranged from 0.2, 0.5, 1.0 and 2.5 weight percent. After attaching sponges with antimicrobial agents together with sponges containing the activator, the same 2 cm wide disks were dissected and tested for antimicrobial activity by a method outlined in Experiments 2 and 3. Staphylococcus aureus was used in agar.

The same collagen sponges with four different dosages of chlorine substances were administered on standardized split thickness wounds inflicted in male Yorkshire pigs, 40 lb. weight. The method used was that of Chvapil et al (1987). In principle, in anesthetized pigs the skin was cleaned with Betadine and prepped with ethanol. Using an electrokeratome, a total of 20 shallow wounds, 2.2×2.2×0.4 cm were excised on the back of the pig. The wounds were treated with various types of collagen sponges, without (control) or with different doses of chlorine dioxide. After administration of the dressing onto the wound, the sponge was moistened with 0.5 ml sterile saline, and covered with adhesive film (Op-site, Smith and Nephew). After 56 hours, the dressing were removed, the wounds excised and processed for histology, 8 random sections were made of each wound and hematoxylin-eosin stained sections were evaluated for the presence of the epithelial cover on the wound surface. The percent of epithelial cover from the total length of the wound was evaluated. If the results are expressed in percent change of the epithelialization as compared to control wounds, it becomes clear that only the highest dose of chlorine dioxide treated sponges statistically significantly inhibited the wound healing.

Dressings containing 1% chlorine-containing compounds had no or minimal adverse effect on epithelial cell growth, still at this dose a striking antimicrobial activity was seen by the inhibition zone (see Table II). During the various steps of manufacturing the final wound dressing, the content of the chlorine compounds was reduced by approximately 50%. It was found that this loss is attributed mainly to freeze drying in vacuum. The actual content of the major chlorine-containing compound ($NaClO_2$) in the final lyophilized sponge was found to be 100–200 $\mu$moles/inch$^2$ of the dressing.

TABLE II

EFFECT OF VARIOUS DOSE OF CHLORINE-ACTIVE COMPONENTS IN COLLAGEN SPONGE WOUND DRESSING ON THE BACTERIAL GROWTH AND RATE OF EPITHELIALIZATION OF SHALLOW WOUNDS IN PIG MODEL

| Concentrate % | Antimicrobial Inhibition Zone[2] (cm) | Effect on Healing[1] (% Inhibition) |
|---|---|---|
| 0 | 0 | 0 |
| 0.2 | 2–5 | 0 |
| 0.5 | 7–10* | 0 |
| 1 | 10–11* | 0–5 |
| 2.5 | 11–12* | 25–30* |

*Refers to statistical significant inhibition at $p < 0.01$.
[1]Data presented in % of change from control values and are average of 3 wounds analysis for each treatment modality
[2]The lowest and highest value (range) of inhibition zone is shown.

What is claimed is:

1. A method of treating a wound area in a mammal, which method comprises:
   a) providing an antimicrobial wound dressing having a first layer of retaining material which includes an antimicrobial-effective amount of a dry, stabilized chlorine dioxide and a second adjacent layer of a retaining material which includes a dermatologically-acceptable dry acidic compound in an amount effective to activate the dry chlorine dioxide; and
   b) applying the first layer of the antimicrobial wound dressing against the wound area and to permit the presence of moisture from the wound area to activate the dry acid compound and the dry chlorine dioxide to produce an antimicrobial, gaseous chlorine dioxide to treat the wound area.

2. The method of claim 1 which includes applying a layer of a vapor impermeable material to the surface of the second layer to retain the moisture from the wound area within the antimicrobial dressing.

3. The method of claim 1 which includes applying a layer of moisture-permeable adhesive to retain the surfaces of the first and second layer together.

4. The method of claim 1 wherein the retaining material comprises collagen.

5. The method of claim 1 wherein the antimicrobial amount of the dry chlorine dioxide comprises from about 0.5 to 2.5 weight percent of the first layer.

6. The method of claim 1 wherein the dry acid compound is selected from the group consisting of ascorbic acid, tartaric acid, citric acid and boric acid.

7. The method of claim 1 which includes sealing the first layer employing a removable, impermeable sealing strip and removing the sealing strip from the first layer just prior to application of the first layer to the wound area.

8. The method of claim 1 wherein the dry, stabilized chlorine dioxide comprises a lyophilized chlorine dioxide.

* * * * *